United States Patent
Ding

(10) Patent No.: US 9,044,750 B2
(45) Date of Patent: Jun. 2, 2015

(54) PIPETTE AND A NUCLEIC ACID PURIFICATION APPARATUS

(71) Applicant: OME TECHNOLOGY CO., LTD., New Taipei (TW)

(72) Inventor: Shih-Hung Ding, New Taipei (TW)

(73) Assignee: OME Technology Co., Ltd., New Taipei (TW)

( * ) Notice: Subject to any disclaimer, the term of this patent is extended or adjusted under 35 U.S.C. 154(b) by 111 days.

(21) Appl. No.: 13/956,535

(22) Filed: Aug. 1, 2013

(65) Prior Publication Data

US 2015/0037227 A1 Feb. 5, 2015

(51) Int. Cl.
*B01L 3/02* (2006.01)

(52) U.S. Cl.
CPC .................... *B01L 3/0293* (2013.01)

(58) Field of Classification Search
CPC ......... B01L 3/02; B01L 3/026; B01L 3/0234; B01L 2/0241; B01L 3/0275; B01L 3/0289; B01L 2200/0631; B01L 2200/0668; B01L 3/021; B01L 3/0293; B01L 3/027; G01N 35/1065
USPC ......... 422/501, 509, 515, 518, 521, 526–527, 422/63, 65, 68.1; 73/863.32, 864, 864.01, 73/864.11, 864.13, 864.16, 864.17, 73/864.23, 864.24, 864.25
See application file for complete search history.

(56) References Cited

U.S. PATENT DOCUMENTS

| | | | | |
|---|---|---|---|---|
| 4,084,730 | A | * | 4/1978 | Franke et al. ............... 73/864.13 |
| 5,726,363 | A | * | 3/1998 | Kalidindi .................... 73/864.14 |
| 6,019,004 | A | * | 2/2000 | Conley et al. .............. 73/864.16 |
| 6,989,131 | B2 | * | 1/2006 | Karlsson et al. .............. 422/528 |
| 7,682,818 | B2 | * | 3/2010 | Mori et al. ................. 435/287.2 |
| 8,337,782 | B2 | * | 12/2012 | Bensley ......................... 422/544 |
| 2002/0146353 | A1 | * | 10/2002 | Bevirt et al. .................. 422/100 |
| 2003/0101831 | A1 | * | 6/2003 | Viot ............................ 73/864.01 |
| 2006/0093527 | A1 | * | 5/2006 | Buss ............................. 422/101 |
| 2010/0043575 | A1 | * | 2/2010 | Tajima ....................... 73/864.11 |
| 2010/0247378 | A1 | * | 9/2010 | Cerra et al. ..................... 422/67 |
| 2011/0027149 | A1 | * | 2/2011 | Uldry ............................ 422/501 |
| 2011/0242530 | A1 | * | 10/2011 | Tuli et al. ...................... 356/300 |
| 2012/0039768 | A1 | * | 2/2012 | Strzelczyk .................... 422/501 |

* cited by examiner

*Primary Examiner* — Brian R Gordon
(74) *Attorney, Agent, or Firm* — Rosenberg, Klein & Lee

(57) ABSTRACT

The present disclosure includes a nucleic acid purification apparatus and a pipette, the pipette comprises: a tubular body, at least a gas seal ring, a nut, and a shaft. A first opening and second opening arranged at two ends of the tubular body air communicable with the tubular body, thus forming a main chamber. The gas seal ring is disposed in a seal slot arranged proximate to the second opening. The nut is coupled to the second opening and has portions forming a cavity air communicable with the nut and second opening. An opening has a pressing edge. The shaft can movably dispose in the tubular body and the nut. The pressing edge presses against the gas seal ring via the firm coupling of the nut onto the second opening. As a result, individual adjustment can provide the optimum airtightness in nucleic acid purification devices.

18 Claims, 7 Drawing Sheets

PIPETTE AND A NUCLEIC ACID PURIFICATION APPARATUS

BACKGROUND OF THE INVENTION

1. Field of the Invention

The instant disclosure relates to a pipette and a nucleic acid purification apparatus, in particular, to a nucleic acid purification apparatus using a pipette capable of fine tuning the extent of airtightness, and stably drawing and injecting liquids.

2. Description of Related Art

For nucleic acid purification of bulk volume, a plurality of pipettes is necessary in order to complete the complex procedures, such as drawing and injection, during the nucleic acid purification process. Generally during the purification process, one pipette is assigned to draw reagents. The reagents are then injected into each biological sample to be purified.

In general, a pipette is used for various sources of specimen samples in order to proceed with the nucleic acid purification. Conventional method molds a plurality of pipettes into a pipette module, in which a majority of the structure is integrally formed. Specifically, individual tuning of the airtightness or disassembly of each pipette is nearly impossible. As a result, after an extended period of operation, at least one or two pipettes of the pipette module begin to show signs of poor airtightness. However, since individual repair on or disassembly of each faulty pipette is nearly impossible, disassembly of the entire pipette module is necessary for the repairment of a few faulty pipettes, which leads to maintenance nuisance and cost. Furthermore, manufacturing of conventional pipette module has a certain degree of difficulty due to the yield consideration for each pipette. If any part (specifically pipette) demonstrates defects, rework cost similarly increases.

To address the above issues, the inventor strives via associated experience and research to present the instant disclosure, which can effectively improve the limitation described above.

SUMMARY OF THE INVENTION

The object of the instant disclosure is to provide a nucleic acid purification apparatus and a pipette to improve upon the conventional pipette maintenance nuisance.

In order to achieve the aforementioned objects, according to an embodiment of the instant disclosure, a pipette is provided which includes a tubular body, at least one gas seal ring, a nut and a shaft. Two ends of the tubular body are respectively formed with a first opening and a second opening air communicable with one another and forming a main chamber in the tubular body. The tubular body includes an inner wall and an outer wall. The gas seal ring is disposed in a seal slot formed on the inner wall proximate to the second opening. The nut is coupled to the outer wall proximate to the second opening. The nut is formed with a cavity therein air communicable with the second opening and an opening oriented towards the tubular body. The nut includes a pressing edge formed therein proximate to the opening. The shaft is movably disposed in the main chamber and the cavity. The pressing edge presses against the gas seal ring via the firm coupling between the nut and the second opening such that the gas seal ring is compressed and a ring inner edge of the seal ring expands towards the shaft to firmly abut the shaft body of the shaft.

The instant disclosure also provides a nucleic acid purification apparatus including a plurality of the aforementioned pipettes, a suction control module, a lifting module, a reagent placement module, and a magnetic module. The suction control module includes a pipette rack having a top plate and a bottom plate. The plurality of pipettes is disposed between the top plate and the bottom plate. The top plate is coupled to the shaft such that the shaft is driven to displace in and out of the main chamber. The bottom plate has a retracting member which recedes the pipette tip. The lifting module controls the ascension and descension of the pipette rack. The reagent placement module has a translational displacement module and a tube rack. The translational displacement module controls the translation displacement of the reagent placement module below the suction control module. The tube rack is formed with a plurality of retaining openings to retain a plurality of test tubes. The magnetic module is configured below the pipette rack proximate to the test tubes or the reagent placement module to magnetically attract a magnetic bead labeled cell in the presence of a tube wall.

With the aforementioned structure of the nut and the gas seal ring, airtightness of each pipette can be adjusted and optimized. The instant disclosure can improve upon the maintenance nuisance and the manufacturing yield of the pipette. Different from the conventional arts, when a plurality of pipettes are applied to the aforementioned pipette module, the instant disclosure provides a pipette which can be individually disassembled, adjusted and repaired from a plurality of pipettes if the pipette fails to provide preferred hermetic sealing.

In order to further understand the instant disclosure, the following embodiments and illustrations are provided. However, the detailed description and drawings are merely illustrative of the disclosure, rather than limiting the scope being defined by the appended claims and equivalents thereof.

DETAILED DESCRIPTION OF THE PREFERRED EMBODIMENTS

Figure 1A:
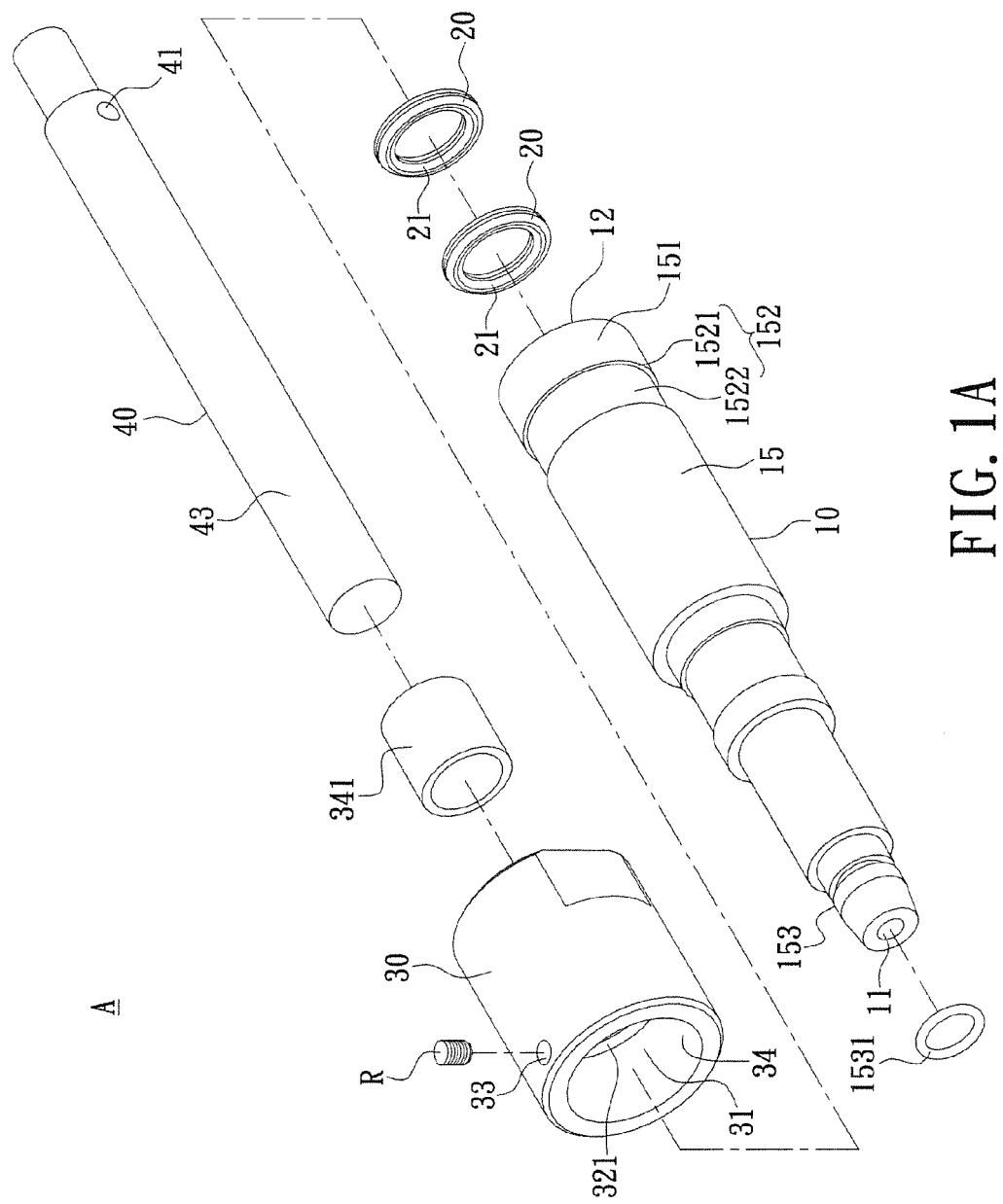
FIG. 1A is an exploded view of a pipette in accordance with the instant disclosure.
Figure 1B:
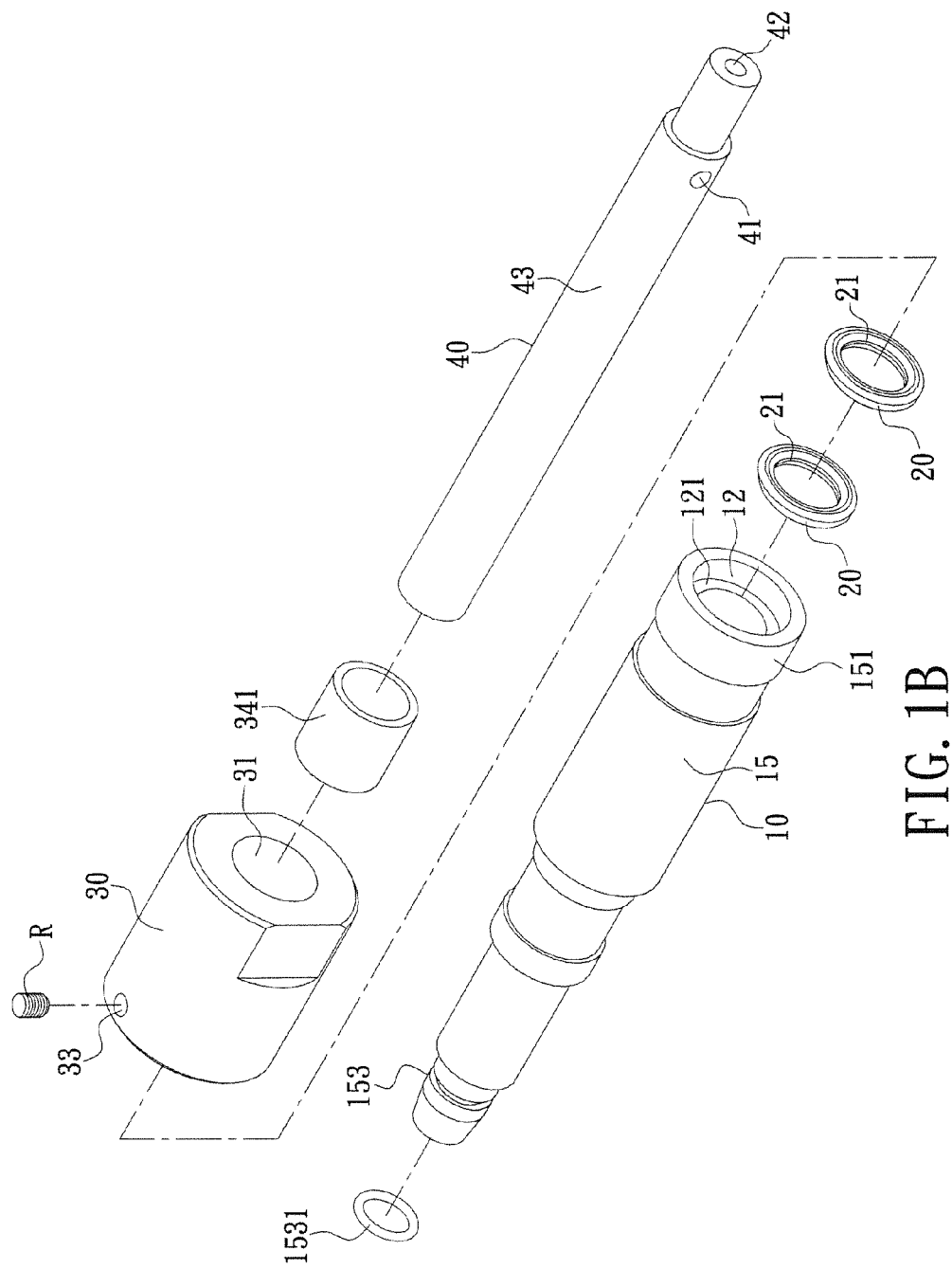
FIG. 1B is a second exploded view of the pipette in accordance with the instant disclosure.

The aforementioned illustrations and detailed descriptions are exemplarities for the purpose of further explaining the scope of the instant disclosure. Other objectives and advantages related to the instant disclosure will be illustrated in the subsequent descriptions and appended drawings.

Please refer to FIGS. 1A, 1B, 3A, and 3B. The instant disclosure provides a pipette A including a tubular body 10, at least one gas seal ring 20, a nut 30 and a shaft 40.

Two ends of the tubular body 10 are respectively formed with a first opening 11 and a second opening 12 air communicable to one another. The tubular body 10 is formed with a main chamber 13 therein. The tubular body 10 has an inner wall 14. The inner wall 14 has an inner fixing wall 141 proximate to the first opening 11 radially extended towards the center of the tubular body 10. The tubular body 10 also has an outer wall 15.

Figure 3A:
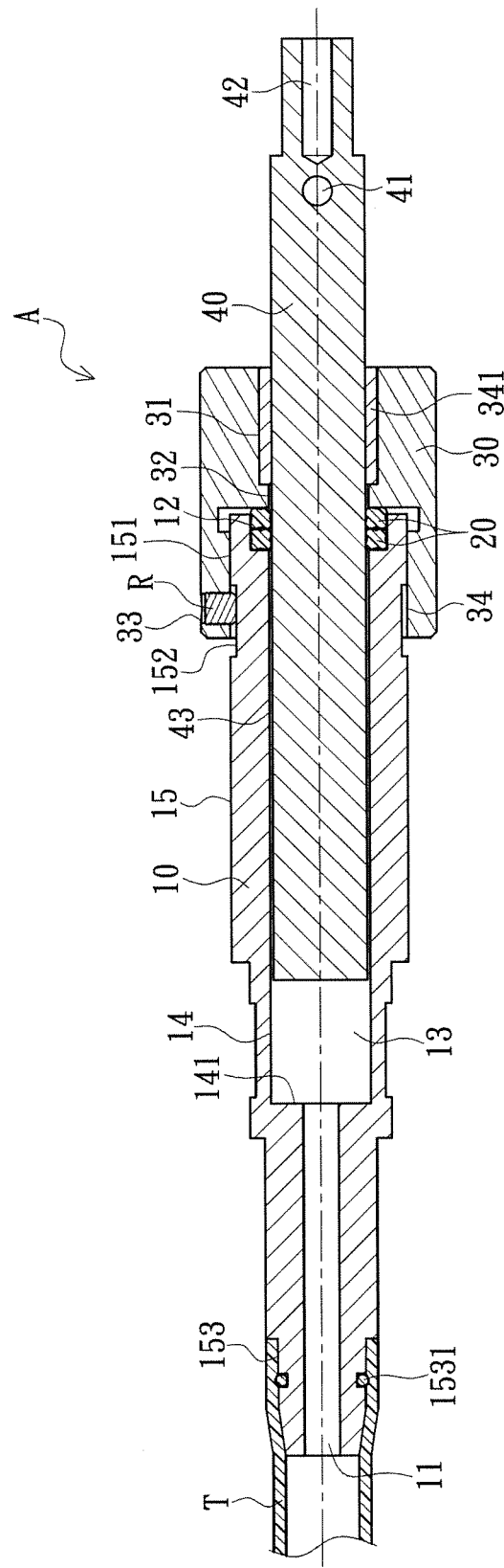
FIG. 3A is a cross-sectional view of the pipette in accordance with the instant disclosure.
Figure 3B:
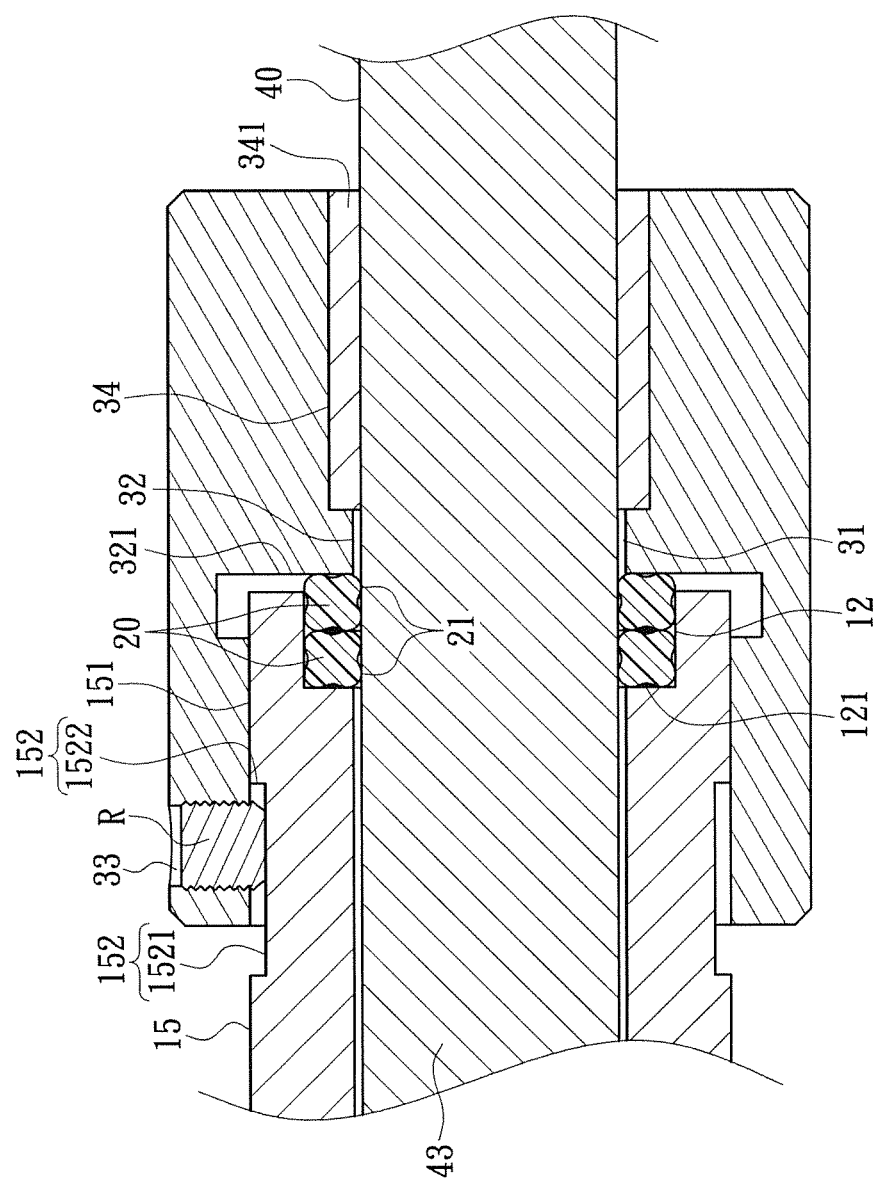
FIG. 3B is a detailed cross-sectional view of the pipette in accordance with the instant disclosure.
Figure 4:
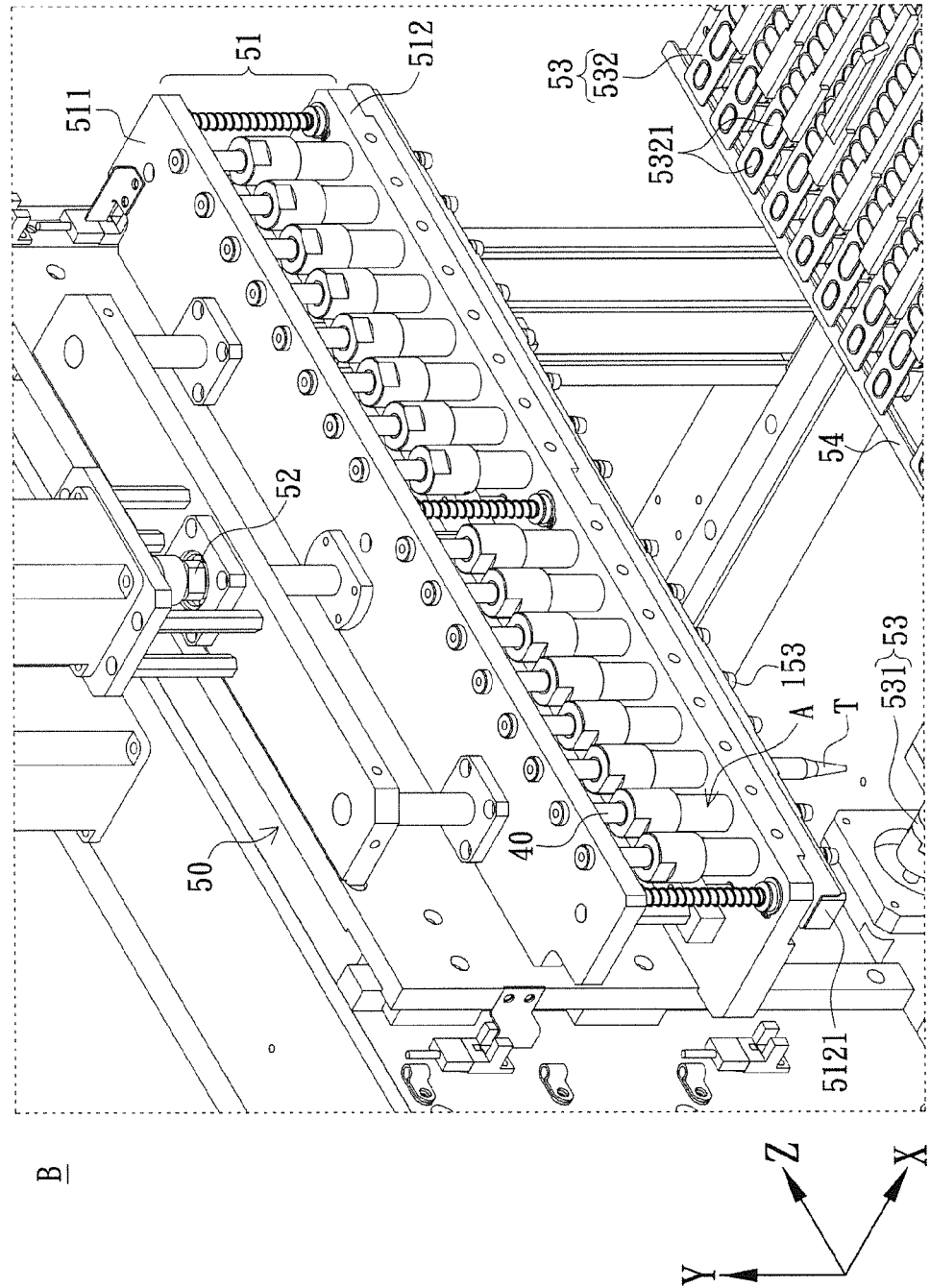
FIG. 4 is a perspective view illustrating the operation of the nucleic acid purification apparatus and the pipette in accordance with the instant disclosure.

Moreover, as illustrated in FIG. 3A, the outer wall 15 sequentially includes from right to left a threaded portion 151 and a groove 152 proximate to the second opening 12 along the tubular body 10. (An inner edge of the groove 152 is defined as a fixing portion 1522.) The outer wall 15 has a coupling portion 153 arranged proximate to an end of the tubular body 10 near the first opening 11. The periphery of the coupling portion 153 has a sealing member 1531. The coupling portion 153 can be coupled to a pipette tip T. The sealing member 1531 is used to strengthen the degree of hermetic coupling between the pipette tip T and the coupling portion 153.

The gas seal ring 20 is an elastic plastic part which is conformingly disposed in a seal slot 121 formed on the inner wall proximate to the second opening 12.

The nut 30 is firmly coupled to the tubular body 10 at the second opening 12. The nut has a nut threaded portion (not labeled) corresponding to the threaded portion 151. The nut 30 is also formed with a cavity 31 air communicable with the second opening 12. The nut 30 also has an opening 32 oriented towards the tubular body 10, the nut 30 including a pressing edge 321 formed therein proximate to the opening 32.

The shaft 40 preferably resembles a rod-shaped part or a pillar-shaped piston. In the instant embodiment, the shaft 40 includes a side port 41, a shaft opening 42, and a shaft body 43. The side port 41 is transversely formed on an end of the shaft body 43 of the shaft 40 distal from the first opening 11 or on an end of the shaft body 43 of the shaft 40 proximate to the tubular body 10.

The shaft opening 42 and the side port 41 are arranged on the same end of the shaft 40. The side port 41 is transversely arranged while the shaft opening 42 is arranged laterally along the shaft body 43, which facilitates assembly between components.

The shaft 40 can be movably disposed in the main chamber 13 and the cavity 31. When the shaft 40 is inserted into the cavity 31 and the main chamber 13, the pressing edge 321 presses against the gas seal ring 20 via the firm coupling between the nut 30 and the second opening 12. Consequently, the gas seal ring 20 is compressed and the ring inner edge 21 of the seal ring 20 expands towards the shaft 40 to firmly abut the shaft body 43 of the shaft 40. As a result, the firm coupling is strengthened between the seal ring 20 and the shaft body 43 of the shaft 40, which facilitates hermetic sealing. In the preferred embodiment, two gas seal rings 20 are preferred, but are not limited herein.

When the instant disclosure draws reagent solutions, the nut 30 can be loosely coupled to an end of the tubular body 10 while the seal ring 20 is coupled to the second opening 12 of the tubular body 10, and the pipette tip T is mounted on and in an interferential fit with the coupling portion 153. The shaft 40 is inserted through the cavity 31 and the main chamber 13. The shaft 40 can be positioned in the cavity 31 or the main chamber 13 to abut the inner fixing wall 141. Since the seal ring 20 and the sealing member 1531 respectively forms a hermetic seal with the shaft body 43 of the shaft 40 and an inner wall of the pipette tip T, when the pipette tip T is dipped to liquid surface (not shown in figures), the shaft 40 can be retracted towards the second opening 12. Due to the pressure difference between the atmosphere and the interior of the tubular body 10, desired liquids can be drawn into the pipette tip.

Preferably, the seal ring 20 can orient towards the second opening 12 and partially protrude from the second opening 12 such that the pressing edge 321 can generate relatively larger pressure on the seal ring 20 when the nut 30 is firmly and interferentially fitted with the second opening 12. Moreover, the pressing edge 321 can also be a protrusion (not shown in figures) formed along the periphery of the opening 32. With the protrusion, partial volume of the overall volume or space is occupied such that when the nut 30 is firmly fixed, the seal ring 20 can be further compressed and deformed. Moreover, the ring inner edge 21 further expands towards shaft 40 such that when the pipette A is coupled with the shaft 40, the seal ring 20 is further compressed onto the shaft body 43 of the shaft 40. Furthermore, the outer surface of the nut 30 is formed with a fixing slot 33 transversely arranged thereon. The fixing slot 33 correspondingly aligns with the groove 152. The fixing slot 33 can be mated with a fixing member R such that the fixing member R presses against (a recessed surface 1521 of) the groove 152, thus, the nut 30 is fixed. Moreover, the fixing portion 1522 is used for interferential fit with the fixing member R or a portion of the groove 152 proximate to the second opening 12 such that when the fixing member R is mated to the fixing slot 33, the nut 30 cannot be conveniently decoupled due to the interference between the fixing member R and the (fixing portion 1522 of the) groove 152.

Preferably, the cavity 31 of the nut 30 is defined by a nut inner wall 34. The nut inner wall 34 has a guiding member 341 which is preferably an elastic plastic part but not limited herein. When the shaft 40 is displaced in and out within the main chamber 13 and the cavity 31, the motion is similar to the operation of a piston. Since the guiding member 341 abuts the shaft body 43 of the shaft 40, the shaft 40 is obviated from bending during the piston-like movement and is supported to maintain relatively linear piston-like movement. In other words, the guiding member 341 can prevent improper structural fitting during the assembly of components and maintain proper movements between components. Namely, the guiding member 341 maintains proper structural fitting or movements between components and can also facilitate firm coupling between the seal ring 20 and the shaft body 43 to enhance hermetic sealing. In another words, the guiding member 341 can guide the shaft 40 to maintain the firm coupling between the shaft 40 and the seal ring 20.

Since the nut 30 provides hermetic coupling between seal ring 20 and the shaft 40 via screwing, the hermetic coupling can be adjusted based on the extent of tightening. In the instant embodiment, the seal ring 20 is the main factor in terms of airtightness. However, the seal ring 20 suffers from fatigue and aging due to extended use. Since the screwed hermetic coupling provided by the instant disclosure can adjust the degree of airtightness, the extent of tightening can be relatively lowered before the aging of the seal ring 20 occurs so that the usable life of the seal ring 20 can be extended to delay aging. Even after the seal ring 20 ages, users can apply even larger extent of tightening on the nut 30 to enhance firm coupling between the seal ring 20 and the shaft body 43, thus, rendering a stronger hermetic seal. As a result, material cost is saved.

In order to achieve the most preferred hermetic sealing, oil or grease, having relatively high viscosity and low mobility such as oil seal and the hermetic oil, can be coated between the shaft 40 or the shaft body 43 and the seal ring 20 or the guiding member 341 of the instant disclosure such that oil or grease can form a robust film between components and prevent air from flowing through gaps formed between components. Moreover, oil or grease can provide lubrication to minimize friction between components, thus, prevent wear and tear and facilitate smooth operations.

Figure 2A:
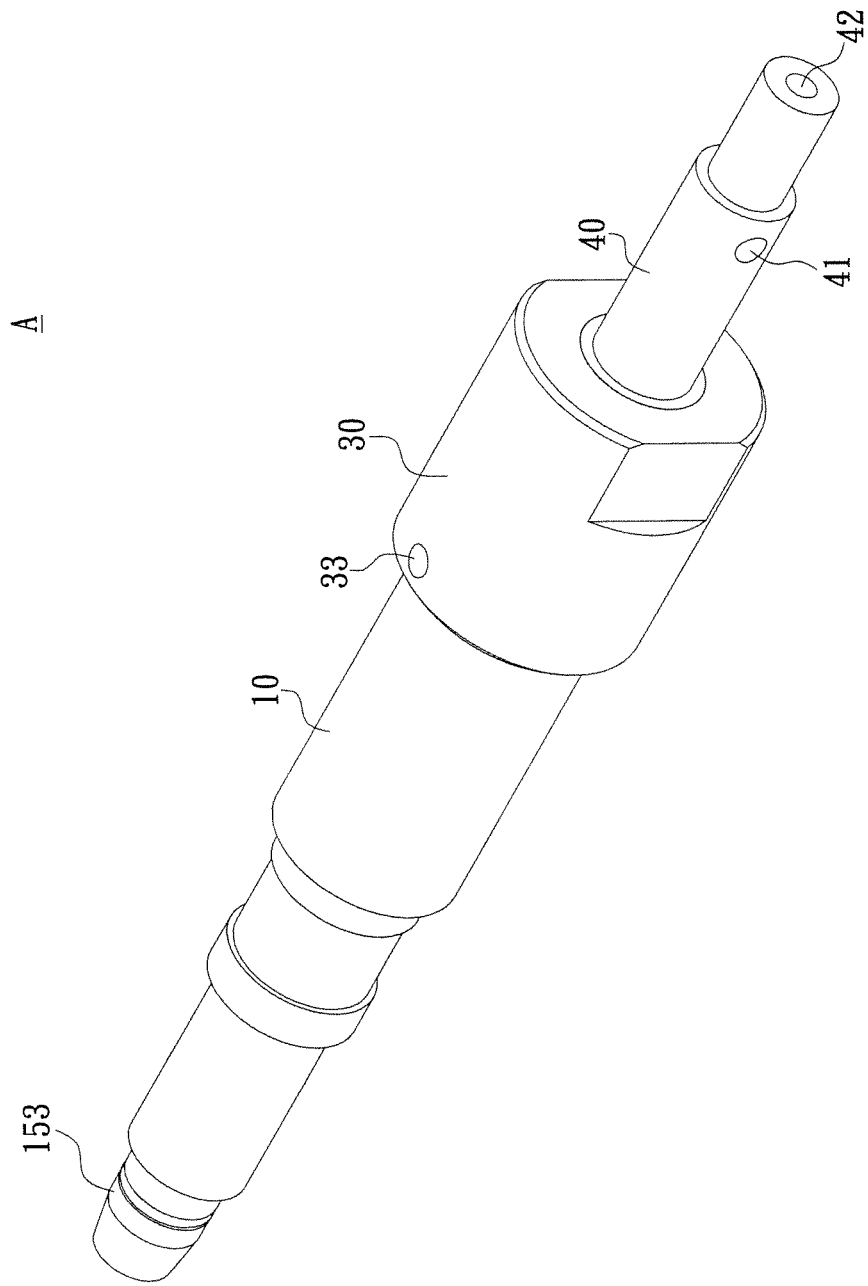
FIG. 2A is an assembled view of the pipette in accordance with the instant disclosure.
Figure 2B:
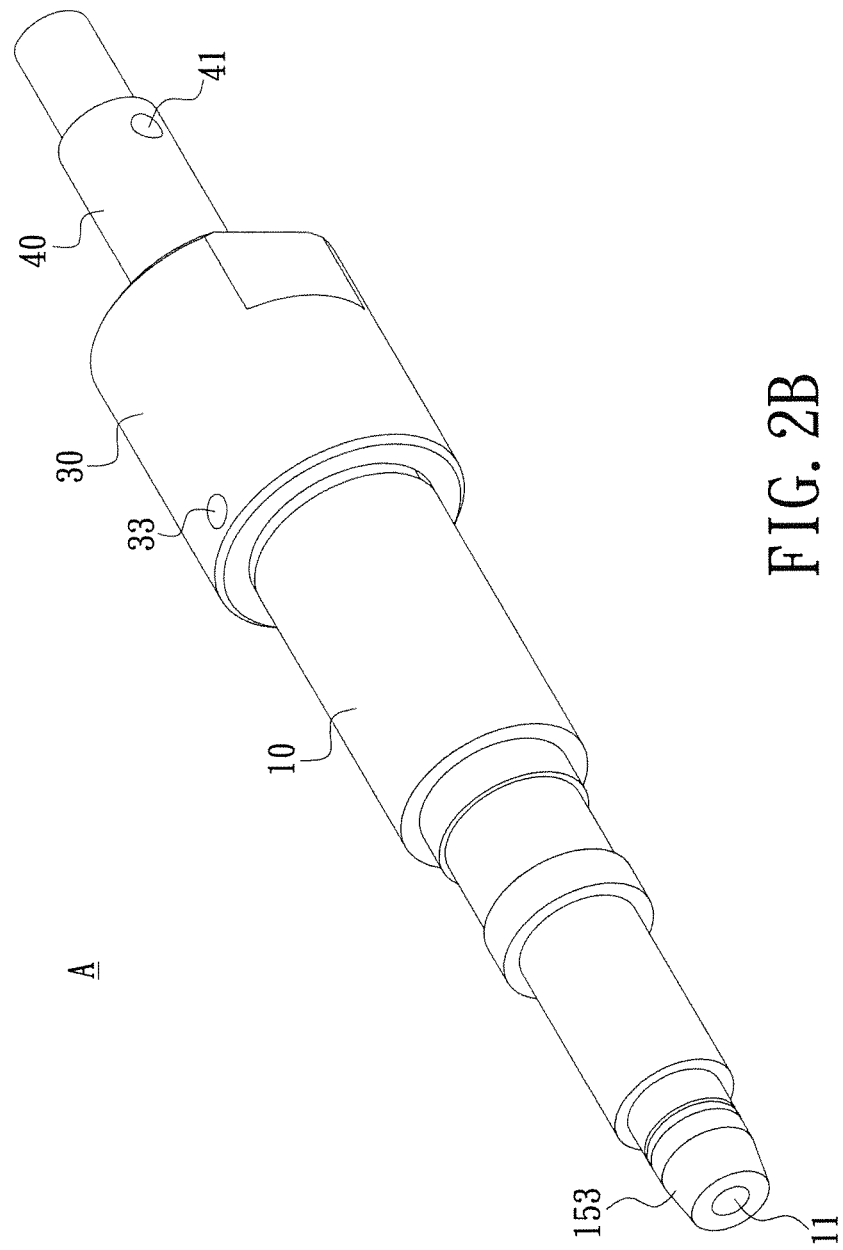
FIG. 2B is a second assembled view of the pipette in accordance with the instant disclosure.

Please refer to FIGS. 2A, 2B, and 3A. After adjusting the hermetic seal between the shaft body 43 of the shaft 40 and the seal ring 20 in the pipette A, the extent of airtightness can be tested before use. In general, the first opening 11 can be blocked in advance, and then a force can be applied to partially pull the shaft 40 out of the pipette A. The pulling force is usually proportional to the hermetic sealing. When the pulling force is larger than the critical tension such that the airtight seal within the pipette A breaks down, the shaft 40 can be smoothly pulled out. At such moment, the critical tension can infer the airtightness provided by the seal ring 20 and the entire pipette A. Alternatively, a pressure gauge can be similarly applied to the first opening 11. Then by advancing the shaft 40, the maximum pressure in the airtight pipette A can be determined. When the internal pressure is larger than the critical pressure such that the airtight seal within the pipette A breaks down, the shaft 40 can be smoothly push towards the cavity in the pipette A. At such moment, the critical pressure can infer the airtightness provided by the seal ring 20 and the entire pipette A. Generally, the extent of airtightness is usually proportional to the required pressure.

The instant disclosure further provides a nucleic acid purification apparatus B which includes a plurality of pipettes A as aforementioned, a suction control module 50 including a pipette rack 51, a lifting module 52 controlling the ascension and descension of the pipette rack 51, a reagent placement module 53 and a magnetic module 54.

The pipette rack 51 preferably includes a top plate 511 and a bottom plate 512 but not limited herein. The top plate 511 and the bottom plate 512 are preferably formed with corresponding fixing opening (not shown in figures) but no limited herein. The plurality of pipettes A is disposed between the top plate 511 and the bottom plate 512. The top plate 511 can mechanically couple to the side port 41 of the shaft 40 such that the shaft 40 is movably disposed in the main chamber 13. The bottom plate 512 has a retracting member 5121 configured below the bottom plate 512. The retracting member 5121 presses down, longitudinally interferes with the wall of pipette tip T (not shown in figures), and recedes the pipette tip T which is already mated to the coupling portion 153.

The lifting module 52 can mechanically control the translational movement of the pipette rack 51 along the Y direction, thus, the height between the pipette A or pipette tip T and the corresponding reagent placement module 53 can be adjusted.

The reagent placement module 53 has a translational displacement module 531 and a tube rack 532. The translational displacement module 531 controls the translation displacement of the reagent placement module 53 along the X and Z direction below the pipette rack 51. The tube rack 532 is formed with a plurality of retaining openings 5321, which retains a plurality of test tubes (not shown in figures). However, the test tubes disclosed in the instant embodiment are not limited to conventional test tubes, but may also include centrifuge tubes of various volumes. Preferred example is a 1.5 mL micro-centrifuge tube (Eppendorf), but not limited herein.

The magnetic module 54 is configured below the pipette rack 51 proximate to the test tubes or the reagent placement module 53. The magnetic module 54 can magnetically attract a magnetic bead labeled cell in the presence of the tube wall such that purified target cells can be reserved during the nucleic acid purification process.

In summary, the instant disclosure provides fine individual adjustments to the airtightness of pipette A during operation. As a result, malfunction of individual unit will not affect the overall process, which requires the disassembly of the entire module. Thus, the instant disclosure is easy to maintain and cost effective. Moreover, with the fine individual adjustments, rework is minimized during manufacturing, which prevents unnecessary material usage.

The figures and descriptions supra set forth illustrated the preferred embodiments of the instant disclosure; however, the characteristics of the instant disclosure are by no means restricted thereto. All changes, alternations, combinations or modifications conveniently considered by those skilled in the art are deemed to be encompassed within the scope of the instant disclosure delineated by the following claims.

What is claimed is:

1. A pipette, comprising:
   a hollow tubular body, two ends of the tubular body respectively formed with a first opening and a second opening air communicable with one another, the tubular body has an inner wall defining a main chamber therein and an outer wall;
   at least one gas seal ring, each disposed in a seal slot formed on the inner wall proximate to the second opening;
   a nut coupled to the outer wall proximate to the second opening, the nut formed with a cavity air communicable with the second opening and a nut opening oriented towards the tubular body, the nut including a pressing edge formed therein proximate to the nut opening; and
   a shaft including a shaft body and movably disposed in the main chamber and the cavity;
   wherein the pressing edge presses against the at least one gas seal ring via a coupling between the nut and the outer wall such that the at least one gas seal ring is compressed and a ring inner edge of the at least one gas seal ring expands towards the shaft to abut the shaft body.

2. The pipette as recited in claim 1, wherein the at least one gas seal ring partially protrudes from the second opening.

3. The pipette as recited in claim 1, wherein the pressing edge is a protrusion formed within the nut along the periphery of the nut opening.

4. The pipette as recited in claim 1, wherein a portion of the outer wall proximate to the second opening includes a threaded portion and a groove, and an inner edge of the groove is a fixing portion.

5. The pipette as recited in claim 4, wherein the nut comprises a fixing slot extending through to the interior of the nut, the fixing slot correspondingly aligns with the groove, and a fixing member is mated to the fixing slot such that the fixing member presses against the groove.

6. The pipette as recited in claim 5, wherein the fixing member is restricted within the groove.

7. The pipette as recited in claim 1, wherein the cavity is defined by a nut inner wall having a guiding member, the guiding member guides the shaft and maintains a coupling between the shaft and the at least one gas seal ring; and
   the guiding member, the at least one gas seal ring, and the shaft body are coated with hermetic oil.

8. The pipette as recited in claim 1, wherein the outer wall has a coupling portion arranged proximate to the first opening, the coupling portion has a sealing member coupled to a pipette tip.

9. The pipette as recited in claim 1, wherein the shaft has a side port transversely formed on and arranged on an end of the shaft.

10. A nucleic acid purification apparatus, comprising:
a plurality of pipettes, each pipette including:
- a pipette tip;
- a hollow tubular body, two ends of the tubular body respectively formed with a first opening and a second opening air communicable with one another, the tubular body has an inner wall defining a main chamber therein and an outer wall;
- at least one gas seal ring, each disposed in a seal slot formed on the inner wall proximate to the second opening;
- a nut coupled to the outer wall proximate to the second opening, the nut formed with a cavity air communicable with the second opening and a nut opening oriented towards the tubular body, the nut including a pressing edge formed therein proximate to the nut opening; and
- a shaft including a shaft body and movably disposed in the main chamber and the cavity;
- wherein the pressing edge presses against the gas seal ring via a the firm coupling between the nut and the outer wall such that the at least one gas seal ring is compressed and a ring inner edge of the at least one gas seal ring expands towards the shaft to abut the shaft body; and a suction control module including:
- a pipette rack having a top plate and a bottom plate, the plurality of pipettes disposed between the top plate and the bottom plate, the top plate coupled to the shaft such that the shaft is driven to selectively displace in the main chamber, the bottom plate having a retracting member which recedes the pipette tips;
- a lifting module controlling the ascension and descension of the pipette rack;
- a reagent placement module having a translational displacement module and a tube rack, the translational displacement module controlling the translation displacement of the reagent placement module below the suction control module, and the tube rack formed with a plurality of retaining openings to retain a plurality of test tubes; and
- a magnetic module configured below the pipette rack proximate to the test tubes or the reagent placement module to magnetically attract a magnetic bead labeled cell in the presence of a tube wall.

11. The nucleic acid purification apparatus as recited in claim 10, wherein the at least one gas seal ring partially protrudes from the second opening.

12. The nucleic acid purification apparatus as recited in claim 10, wherein the pressing edge is a protrusion formed within the nut along the periphery of the nut opening.

13. The nucleic acid purification apparatus as recited in claim 10, wherein a portion of the outer wall proximate to the second opening includes a threaded portion and a groove, and an inner edge of the groove is a fixing portion.

14. The nucleic acid purification apparatus as recited in claim 13, wherein the nut comprises a fixing slot extending through to the interior of the nut, the fixing slot correspondingly aligns with the groove, and a fixing member is mated to the fixing slot such that the fixing member presses against a recessed surface of the groove.

15. The nucleic acid purification apparatus as recited in claim 14, wherein the fixing member is restricted within the groove.

16. The nucleic acid purification apparatus as recited in claim 10, wherein the cavity is defined by a nut inner wall having a guiding member, the guiding member guides the shaft and maintains a coupling between the shaft and the at least one gas seal ring; and the guiding member, the at least one gas seal ring, and the shaft body are coated with hermetic oil.

17. The nucleic acid purification apparatus as recited in claim 10, wherein the outer wall has a coupling portion arranged proximate to the first opening, the coupling portion has a sealing member coupled to the pipette tip.

18. The nucleic acid purification apparatus as recited in claim 10, wherein the shaft has a side port transversely formed on and arranged on an end of the shaft.

* * * * *